United States Patent [19]

Kazlauskas et al.

[11] Patent Number: 4,940,527

[45] Date of Patent: Jul. 10, 1990

[54] TWO-PART TEST CARTRIDGE FOR CENTRIFUGE

[75] Inventors: Vidas P. Kazlauskas, Waukegan; Roger A. Janczak, Mundelein; Benton A. Durley, III, Antioch, all of Ill.

[73] Assignee: Abbott Laboratories, Abbott Park, Ill.

[21] Appl. No.: 337,011

[22] Filed: Apr. 12, 1989

Related U.S. Application Data

[63] Continuation-in-part of Ser. No. 196,120, May 25, 1988, which is a continuation-in-part of Ser. No. 56,605, Jun. 1, 1987, abandoned.

[51] Int. Cl.⁵ ............................................. G01N 27/403
[52] U.S. Cl. .................................. 204/401; 204/411; 422/72; 422/99
[58] Field of Search ................. 204/401, 411; 422/72, 422/63, 99

[56] References Cited

U.S. PATENT DOCUMENTS

| | | | |
|---|---|---|---|
| 4,397,725 | 8/1983 | Enzer et al. | 204/406 |
| 4,436,610 | 3/1984 | Enzer et al. | 204/400 |
| 4,529,495 | 7/1985 | Marsoner | 204/411 |
| 4,654,127 | 3/1987 | Baker et al. | 204/1 T |
| 4,705,668 | 11/1987 | Kaltenbach et al. | 422/82 |
| 4,726,929 | 2/1988 | Gropper et al. | 422/68 |
| 4,786,394 | 11/1988 | Enzer et al. | 204/401 |
| 4,814,282 | 3/1989 | Holen et al. | 436/165 |

OTHER PUBLICATIONS

Steven G. Schultz et al., Clinical Chem., vol. 31, No. 9, pp. 1457–1463, (1985).

Primary Examiner—G. L. Kaplan
Attorney, Agent, or Firm—Thomas D. Brainard; Richard D. Schmidt

[57] ABSTRACT

A two-part test cartridge for use in a centrifugal analyzer for measuring the concentration of different electrolytes in blood or blood serum samples has one part which is disposable and which is characterized by a sample entry port, one or more filled calibrant chambers, a waste chamber and passages between various chambers; and a second, mating part which is reusable and which is characterized by an ISE, a power supply and circuitry therefor, and a series of chambers and passages adapted for communication with the series of chambers and passages in the disposable part.

12 Claims, 5 Drawing Sheets

TWO-PART TEST CARTRIDGE FOR CENTRIFUGE

This application is a continuation in part of a co-pending, commonly owned U.S. application entitled "Apparatus for Measuring Electrolytes", Ser. No. 196,120, filed May 25, 1988, which is a continuation-in-part of now abandoned application, Ser. No. 056,605, filed June 1, 1987, both of which are incorporated herein by reference.

Other related and commonly assigned applications filed concurrently herewith include: Ser. No. 336,944, now U.S. Pat. No. 4,891,125 relating to a REFERENCE ELECTRODE; Ser. No. 337,007, now U.S. Pat. No. 4,902,399 relating to a miniature ION SELECTIVE ELECTRODE AND METHOD OF MAKING SAME; and another continuation-in part Ser. No. 336,943 of the above-mentioned Ser. No. 196,120, relating to digital electronic aspects of an APPARATUS FOR MEASURING ELECTROLYTES. The entire disclosures of each of the above applications are specifically incorporated herein by reference.

BACKGROUND OF THE INVENTION

This invention relates to apparatus for the testing of electrolytes in blood/blood serum samples and, more specifically, to unit dose test cartridges for use in a centrifugal analyzer wherein the primary sensor is an ion-selective electrode (ISE).

Test cartridges adapted to be removably mounted in one of several test stations disposed near the outer edge of a centrifuge rotor plate for rotation therewith and for rotation relative thereto between at least two angularly spaced positions (two dimensional centrifugation) are known in the art. Schultz, et al., Clin. Chem. 31/9, pp 1457–1463 (1985), describe such a test cartridge used for clinical chemistry determinations in conjunction with the VISION ® centrifugal analyzer (Abbott Laboratories, Abbott Park, IL). Further examples can be found in U.S. Pat. No. 4,788,154 (Guigan), U.S. Pat. No. 4,743,558 (Guigan), EP-A-251,946 (KIS Photo Industries), FR 2,589,240 (KIS Photo Industrie) and EP-A-160,282 (Abbott).

However, specific problems associated with electrolyte determinations by ISEs are not addressed by these prior art cartridges. In particular, cartridges for ISE determinations employ an ISE, a power supply and electronic circuitry for the ISE. For a centrifugal analyzer, a means for transmitting a signal from the ISE or circuitry to the instrument is also required. These components are relatively expensive and should be reused if possible. Cartridges for ISE determinations also require a sample chamber, one or more calibrant chambers, a waste chamber and passages interconnecting these. These components typically cannot be reused and must be disposable. Thus there is a need in the art for a test cartridge having two parts: a reusable portion and a disposable portion.

Two part cartridges are known in the art of centrifugal analyzers. EP-A 251,946 is an example and discloses a test cartridge having a first portion containing a reagent compartment, a mixing chamber and a cuvette. A second portion contains a sample inlet, a separation chamber and a serum outlet. However, this is not adaptable to the ISE situation wherein calibrants and sample must flow from a chamber in the disposable portion to the ISE in the reusable portion and back to the disposable portion to a waste chamber.

It is therefore an object of the present invention to provide a test cartridge which comprises two interfitting portions, one being reusable and the other being disposable, with the ability for a fluid to flow from the disposable to the reusable and back to the disposable.

It is also an object of the present invention to provide a unit dose ISE test cartridge for use in a centrifugal analyzer for testing for electrolytes, such as sodium, potassium, chloride, carbon dioxide, etc. in blood/blood serum samples.

A still further object of the present invention is to provide a two-part test cartridge wherein the ISE and its power supply and circuitry are provided in the reusable portion and a sample port, a waste chamber, and one or more filled and sealed calibrant chambers are provided in the disposable portion.

Yet another object of the present invention is to provide such a two part test cartridge wherein the reusable portion is provided with piercing members for automatically unsealing the calibrant chambers during interconnection of the reusable and disposable portions thereof.

SUMMARY OF THE INVENTION

The present invention relates to a two-part unit dose test cartridge for use in a centrifugal analyzer. The two-part test cartridge comprises a first disposable cartridge portion having a series of compartments and passageways including a sample entry port, an electrolyte exit port, a waste chamber, and one or more chambers containing calibrants. A second reusable cartridge portion is interengageable with said first cartridge portion and has a series of compartments and passageways including an entry port adapted to interfit with said electrolyte exit port of said first cartridge portion and an exit port adapted to interfit with said waste chamber in said first cartridge portion, and means automatically providing communication with said calibrant chamber(s) upon interengagement of said first and second cartridge portions.

Ideally, a pierceable sealing means holds calibrants in their respective chambers until the reusable part is engaged with the disposable, whereupon piercing pins from the reusable part pierce and open the calibrant chambers. It is also preferred that the more expensive components, such as the ISE, the power source, the circuitry and the signal transmitting means, reside in the reusable portion; while the calibrant chambers, sample chamber and waste chamber reside in the disposable portion.

In another aspect, the invention relates to a disposable portion for use with a reusable portion of a test cartridge having at least one sensor and a network of compartments and passageways therein. The disposable portion is interengageable with said reusable portion and comprises a sample entry port, filled calibrant chamber means, a waste chamber, and a network of compartments and passageways adapted for communication with said network in said reusable portion whereby fluid flows from the disposable, into the reusable and back to the disposable.

DESCRIPTION OF A PREFERRED EMBODIMENT

Figure 1:
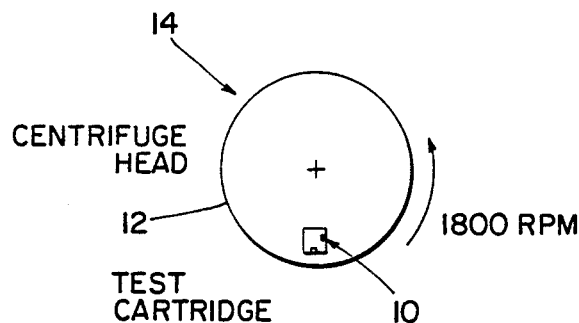
FIG. 1 is a diagrammatic plan view of a centrifugal analyzer rotor head with a two-part unit dose test cartridge embodying the invention rotatably mounted at one station on the outer edge thereof in one of its two angular positions.
Figure 2A:
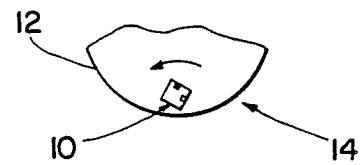
FIGS. 2a and 2b are fragmentary top plan views similar to FIG. 1 showing rotation (FIG. 2a) of the two-part test cartridge into its second angular position (FIG. 2b) on the rotor.
Figure 2B:
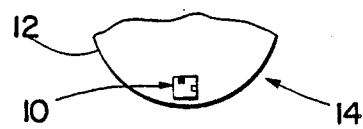

With reference first to FIGS. 1, 2a and 2b, a unit dose test cartridge 10 embodying a preferred form of the present invention is diagrammatically shown mounted in one of several test stations or holders provided adjacent the outer edge of a rotor 12 of a centrifugal analyzer 14 used in a known type automated apparatus. Such an apparatus/test cartridge combination is disclosed in the background references and moves fluids throughout the cartridge in a controlled manner under the influence of centrifugal force applied in two apparent directions by rotation of the cartridge with respect to the rotor.

During testing, the rotor plate 12 rotates at high speeds, typically about 1800 rpm, thereby subjecting fluid samples and calibrants in the test cartridge 10 to severe centrifugal forces approximating $500 \times G$. Under such force, fluids are directed into and out of a labyrinth of passages and chambers provided in the test cartridge 10 according to a predetermined protocol. Although not shown in the drawings, the test cartridge 10 is mounted on the rotor plate 12 in any suitable manner known in the art, as for example, in a self-balancing holder, bucket or cradle, for back and forth rotation relative to the rotor plate 12 between two angular positions positioned about 90° apart.

Figure 3:
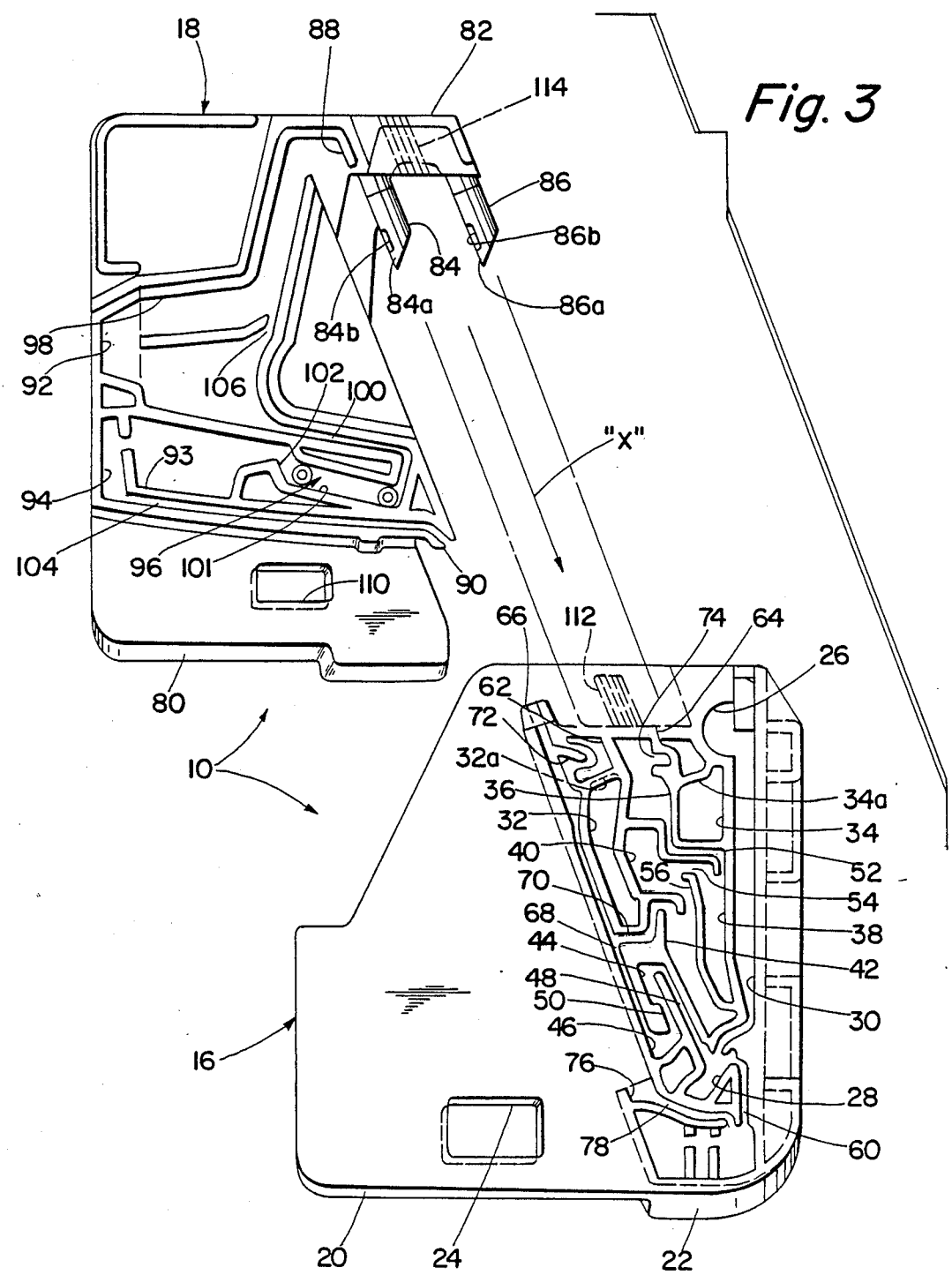
FIG. 3 is a modified top/front perspective view of the two-parts of the test cartridge as aligned for interconnection with the arrow "X" indicating the direction of assembly thereof.

As best shown in FIG. 3, the novel multi-chambered test cartridge 10 of the present invention comprises two interfitting parts, one part 16 being disposable, and the other part 18 being reusable.

The disposable portion 16, as best illustrated in FIG. 3, is characterized by a generally rectangular plate 20 molded of plastic and having rounded corners and an integral housing portion 22 depending from the underside thereof generally along the right-hand side thereof (as viewed in FIG. 3). The plate member 20 serves as a surface for labeling but is provided with an LCD optical opening 24 spaced from the housing portion 22.

A labyrinth of chambers and passages is provided within the housing portion 22 including a blood/blood serum sample well 26, a blood separating chamber 28, and a capillary passage 30 extending between the sample well 26 and the separating chamber 28. Calibrant chambers 32 and 34 are filled at manufacture with appropriate first and second calibrants (or calibrating fluids) for the electrolyte to be assayed and are then sealed. Sealing may be accomplished by installing membrane seals 32a and 34a, but preferably the membrane seals are in place prior to filling the chambers from above and the chambers are sealed by a label or thermoplastic layer as described hereinafter.

First calibrant is a low level calibrant for the specific electrolyte of interest and second calibrant is a high level calibrant. Although the chambers of the preferred embodiment are configured to empty first calibrant, then sample and then second calibrant from the disposable and across the sensor, other variations are possible. For reasons of storage and stability, it is preferred to finish with the high calibrant, which then keeps the sensor moist. As used herein, calibrants may include reagents and or diluents.

First and second sample delay chambers 44 and 46 delay sample in the disposable 16 until the first calibrant is tested. First, second, third and fourth delay chambers 36, 38, 40 and 42 similarly stall the second calibrant in the disposable 16 to allow each fluid to be analyzed sequentially. A passage 48 connects the separating chamber 28 to the first sample delay chamber 44, and a passage 50 connects the first sample delay chamber 44 to the second sample delay chamber 46. Analogously, passage 52 leads from the second calibrant's first delay chamber 36 to the second calibrant's second delay chamber 38; a short passage 54 leads from the second calibrant's second delay chamber 38 to the second calibrant's third delay chamber 40; and a passage 56 leads from the second calibrant's third delay chamber 40 to the second calibrant's fourth delay chamber 42. Each of the delay chambers and passages are carefully arranged so that fluid flows from one to the next under centrifugal force upon each sequential rotation of the cartridge 10 with respect to the rotor 12. Although not evident from the drawings, the depth of the chambers may vary depending on the volumes they are required to hold. Typically, the passages are minute capillary passages that do not extend the full depth of the cartridge.

Figure 4:
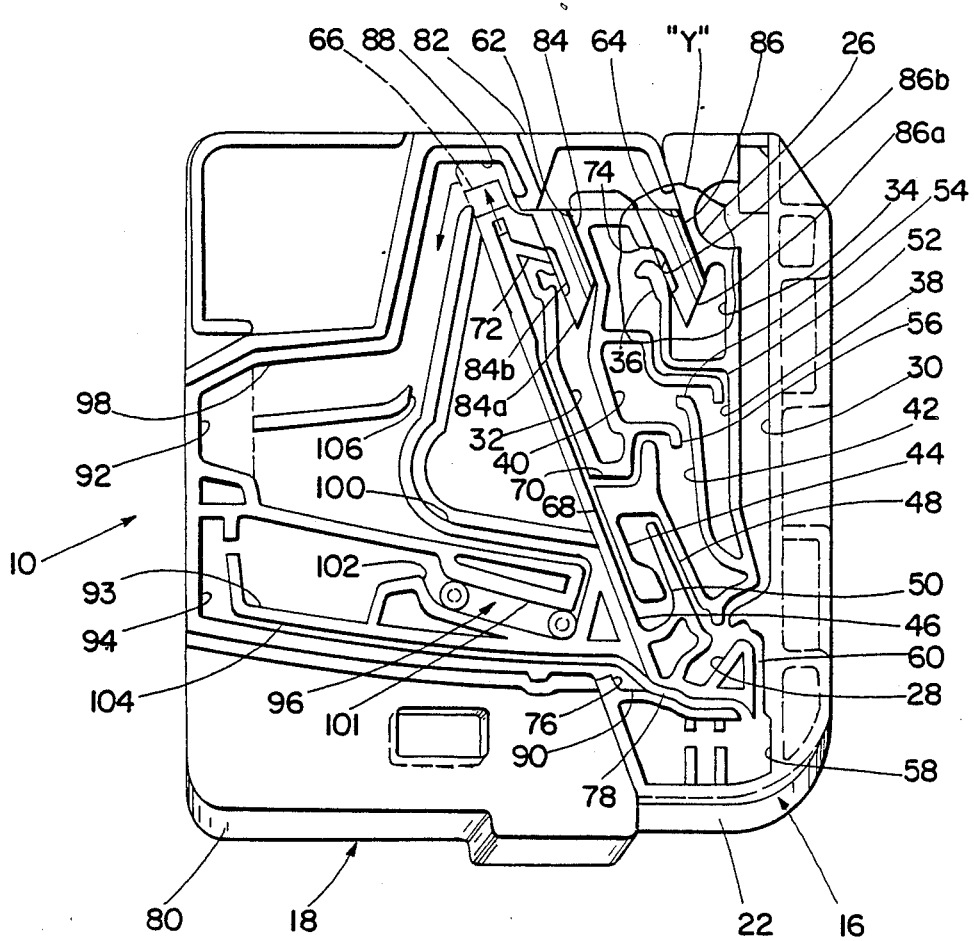
FIG. 4 is a modified top/front perspective view of the two-part test cartridge of FIG. 3 after assembly thereof, and showing fluid flow paths.

At the top of disposable 16 (See FIG. 3), a pair of cylindrically-formed piercer ports 62 and 64 extend parallel to one another and into the housing portion 22. Their inner ends terminate at the sealed entrances to the first and second calibrant chambers 32 and 34, respectively. An exit port 66 provides a fluid outlet from the labyrinth of chambers and passages in the housing portion 22. The port 66 is connected by passage 68 to the sample second delay chamber 46; by passage 70 to the second calibrant's fourth delay chamber 42; and by passage 72 to the piercer port 62 associated with the first calibrant chamber 32. Passage 74 extends between the second calibrant's first delay chamber 36 and the piercer port 64 associated with the second calibrant chamber 34. A funnel-like entry or return port 76 to the housing portion 22 is connected by a passage 78 to a waste chamber 58 (shown in FIG. 4). As will be described in more detail hereinafter, the exit port 66 and the entry or return port 76 engage with corresponding portions of the reusable portion 18 to permit fluid flow from the disposable, to the reusable and back to the disposable.

The waste chamber 58 also receives excess sample from the separating chamber 28 via overflow passage 60.

Figure 5:
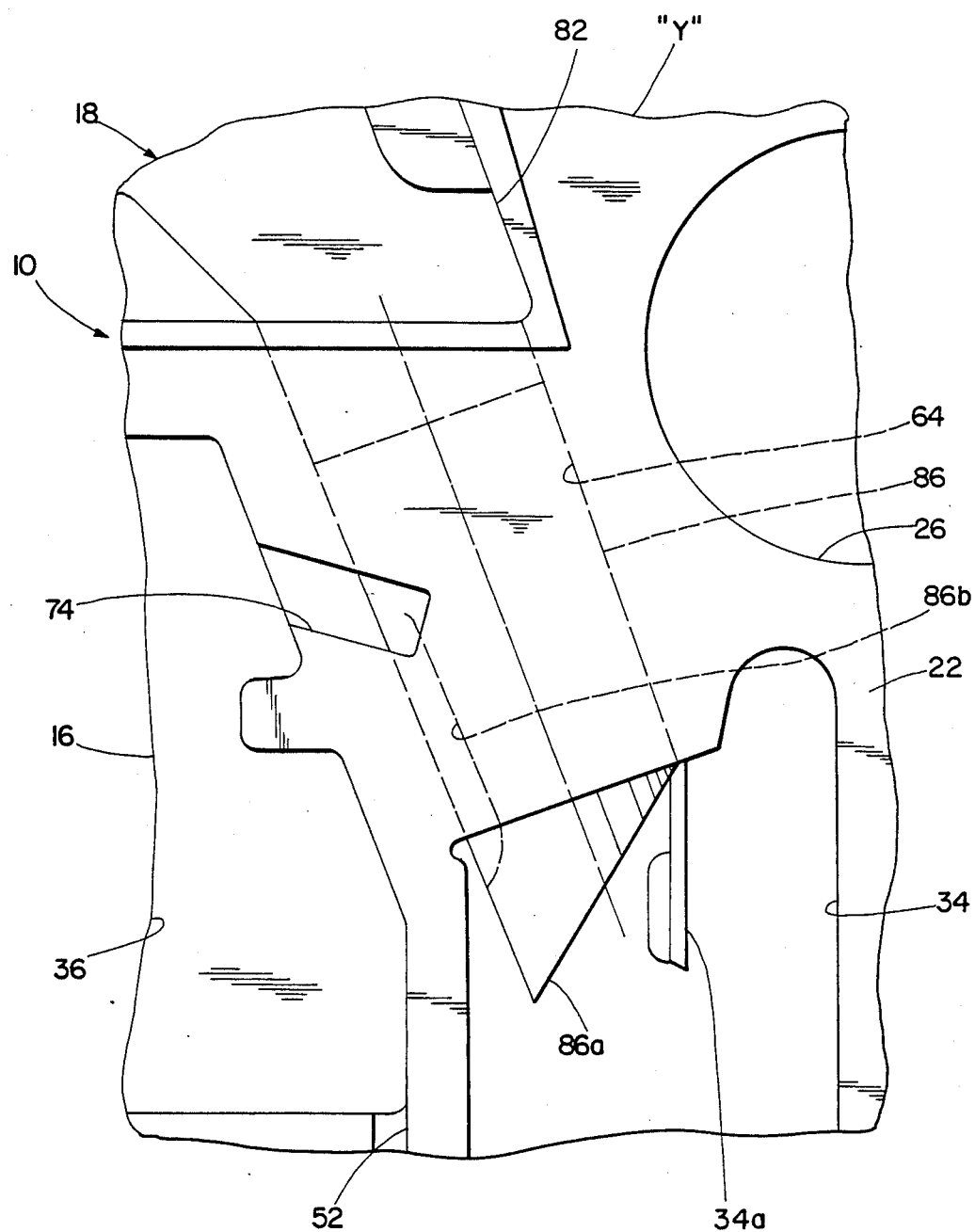
FIG. 5 is an enlarged view of the portion of FIG. 4 defined by line "Y" and showing unsealing of one of the sealed calibrant chambers in the disposable part of the test cartridge by one of the piercing members on the reusable part of the test cartridge.

The reusable portion 18 of the test cartridge 10 is adapted to be interfitted or interengaged with the disposable portion 16 and is characterized by housing the more costly elements of the test cartridge 10. As best illustrated in FIG. 3, the reusable portion 18 is characterized by a three-dimensional housing 80 having a configuration which generally complements the housing portion 22 of the disposable portion 16 to fill out the plate member 20. The housing 80 includes an arm portion 82 which extends over the outer or open ends of the piercer ports 62 and 64. The arm portion 82 is provided with a pair of piercing members 84 and 86 which extend therefrom in parallel relationship and at an angle such that they are aligned for entry into the piercer ports 62 and 64, respectively, upon assembly of the disposable and reusable portions. As shown in FIG. 3, each piercer member 84 and 86 may be provided at its end with a finger or point 84a and 86a for automatically unsealing the sealing membranes 32a and 34a upon assembly. This is illustrated in detail in FIG. 5 with respect to piercer 86 and sealing membrane 34a of the second calibrant chamber 34. The piercing members 84 and 86 are also provided on their outer surfaces with notches 84b and 86b, respectively, which extend longitudinally thereon for a purpose which will be discussed hereinafter.

The housing portion 80 of the reusable portion 18 is provided with a labyrinth of chambers and passages, although less complex than that of the disposable portion 16. This labyrinth includes a funnel like entry port 88 which is situated generally at the juncture of the arm portion 82 and the main body of the housing 80, and an exit port 90. The ports 88 and 90 are adapted to sealingly receive the exit port 66 and the funnel-like entry port 76, respectively, of the disposable portion 16 during assembly of the disposable and reusable portions 16 and 18.

The labyrinth of the housing portion 80 is also characterized by a delay chamber 92 connected to the entry port 88 by a passage 98. For the calibrants, chamber serves merely as a delay; but for the sample, chamber 92 can serve as a hemolysis check. Typical electrolytes being determined by the present invention are present inside blood cells and would affect the readings if cell contents were released. Therefore, it is preferable to check for red pigment from lysed cells by optically examining the sample in the delay chamber 92. This is advantageously accomplished by positioning the delay chamber 92 such that, depending on the orientation, either the chamber 92 or subsequently described LCD 110 aligns with a flash lamp and detector system. An exemplary lamp and detector is described in Schultz, U.S. Pat. No. 4,687,329.

Passage 100 extends from the delay chamber 92 to the sensor assembly 96. In the preferred embodiment the sensor assembly 96 is an ion selective electrode (ISE) system comprising a miniature ISE, a reference electrode, and necessary electronic and optical circuitry therefor. The details of the ISE assembly 96 itself form no part of the present invention but are disclosed in co pending applications, Ser. Nos. 336,943 and 337,007, which are being filed concurrently herewith, the disclosures of which are incorporated herein by reference. One application, Ser. No. 337,007 is entitled "ISE and Method of Making Same", and the other application, Ser. No. 336,944, is entitled "Reference Electrode". For purposes of this application it is not important what type of sensor or how many are used. In a preferred embodiment several sensors may be employed simultaneously to analyze a sample for a plurality of electrolytes (or other parameters). It is important only that a channel, chamber or passage 101 be situated in sensing contact with the sensing elements of the sensor assembly, and that fluids pass through such a channel. An air vent 106 may be provided to equalize pressure between passage 98 and passage 100.

From an outlet of the sensor assembly 96, a passage 102 empties into a pond 93. The pond 93 overflows into delay chamber 94 and passage 104 which leads to the exit port 90. The purpose of the pond is to provide a reservoir of fluid which can be used to replenish the storage fluid left surrounding the sensors. It should be noted that the pond 93 is quite shallow relative to the chamber 94 so that all the fluid retained in the pond will empty into chamber 94 upon rotation of the cartridge as described later.

The housing portion 80 is also provided with an LCD window 110 which, when the two portions 16, 18 are assembled, is aligned with the LCD window 24 in the plate member 20 of the disposable portion 16. The LCD, along with appropriate circuitry, provides a transmitting means to convert and transmit sensor signals to the centrifugal analyzer for readout. The details of this system are disclosed in U.S. application entitled "Apparatus for Measuring Electrolytes", Ser. No. 196,120, filed May 25, 1988, and in a continuation in-part of the above mentioned Ser. No. 196,120, relating to digital electronic aspects of an APPARATUS FOR MEASURING ELECTROLYTES. The entire disclosures of each of the above applications are specifically incorporated herein by reference.

For proper operation of sensitive electronic components, it has been found necessary to shield the components from interference from instrument noise. Shielding is accomplished by applying a metallic coating to appropriate surfaces of the cartridge. It is also advantageous to arrange the fluids portion (e.g., passages 98, 100, 101, 102 and 104 and chambers 92, 93 and 94) of the reusable on one level (e.g. top) of housing 80 and the electronic components on the other level of housing 80.

It is noted that each electrolyte to be tested for in a blood/blood serum sample requires an ISE designed for that particular electrolyte as well as appropriate calibrants therefor. Thus, it is imperative that a disposable for one electrolyte not be matched with a reusable for a different electrolyte. It is preferable, then, that the disposable and reusable test cartridge portions 16 and 18 be coded or keyed to insure against mismatched assembly of a disposable 16 for one electrolyte with a reusable 18 for a different electrolyte. As best illustrated in FIG. 3, a rib-like key 112 is provided on the disposable portion 16 with a mating slot or groove 114 being provided on the arm portion 82 of the reusable portion 18. For different electrolytes, the key 112 on the disposable portion 16 could be shifted varying distances laterally and the slot 114 shifted accordingly. Alternatively, varying numbers of keys 112 and slots 114 could be used.

When the disposable and reusable portions 16 and 18 are slidably assembled, as illustrated in FIG. 3, they are retained in assembled relationship through the combined frictional engagement of the piercing members 84 and 86 in the piercer ports 62 and 64, respectively; the exit ports 66 and 90 in the funnel like entry ports 76 and 88, respectively; and, for lateral stability, the rib-like key 112 in the slot 114. The funnel-like entry ports 76 and 88 ensure that fluid transfer from the disposable portion 16 to the reusable portion 18 and back again (as will be described hereinafter) is accomplished without spillage. It is noted that if, during fabrication of the disposable portion 16 the labyrinth of chambers and passages are left open (for ease of filling or manufacture), a heat sealed membrane or label applied over plate member 20 and housing 22 will provide suitable sealing thereof.

Although the piercing members 84 and 86, or fingers 84a and 86a thereon (see FIGS. 3 and 5), pierce or dislodge the sealing membranes 32a and 34a of the calibrant chambers 32 and 34, respectively, during assembly of the cartridge 10 and it appears that the notches 84b and 86b thereon provide free fluid communication from the chambers 32 and 34 to the passages 72 and 74, respectively, the design is such that such fluid flow is provided only under the application of centrifugal force to the test cartridge 10. Under the force of gravity alone, the surface tension of the fluids is sufficient effectively to impede flow through the minute passages formed by notches 84b and 86b.

Figure 6A:
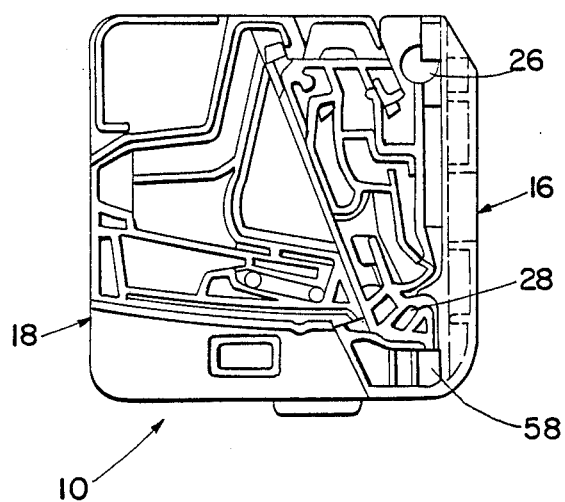
FIGS. 6a through 6g are plan views of the assembled two part test cartridge of the present invention showing its successive angular positions relative to the centrifugal force vector (always downwardly in FIGS. 6a–6g) as the cartridge rotates back and forth between its two programmed angular positions.

In operation, the assembled unit dose test cartridge 10, which includes both a disposable portion 16 and a reusable portion 18, is loaded into a suitable centrifugal analyzer testing instrument 14 onto the rotor plate 12 thereof, a sample of blood/blood serum having been deposited in the sample well 26 thereof. The programmed instrument 14 is activated whereupon the sample is spun down into the separating chamber 28 (FIG. 6a) where the cells and serum or plasma thereof are separated, any excess sample flowing through passage 60 into waste chamber 58.

Figure 6B:
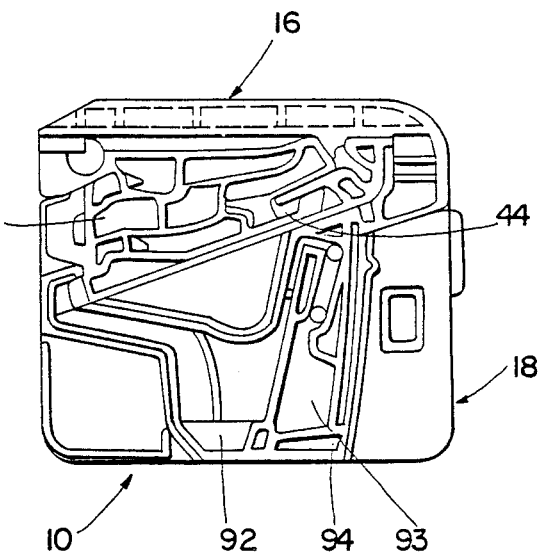

The cartridge 10 is then automatically rotated 90° counterclockwise into its second angular position as shown in FIG. 6b, during continued rotation of the rotor plate 12, whereupon fluids flow simultaneously as follows: (1) the serum or plasma flows through passage 48 into the first sample delay chamber 44; (2) the first calibrant flows out of its chamber 32 through notch 84b, passage 72, disposable exit port 66 and reusable entry port 88, and passage 98 into delay chamber 92; (3) the second calibrant flows out of its chamber 34 through notch 86b and passage 74 into the second calibrant's first delay chamber 36; and (4) any storage fluid left in channel 101 or pond 93 flows into chamber 94.

Figure 6C:
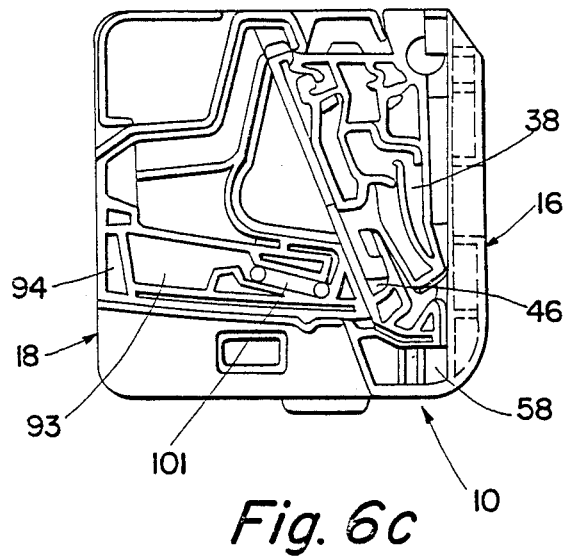

As the cartridge 10 is rotated 90° clockwise back to its original upright position (FIG. 6c) to complete the first of three programmed "rotate-return" cycles, fluid flows simultaneously as follows: (1) sample flows from the first sample delay chamber 44 through passage 50 into the second sample delay chamber 46; (2) the first calibrant flows from delay chamber 92 through passage 100 into channel 101 of the ISE sub-assembly 96 for first calibration of the sensor, with excess continuing into pond 93; (3) the second calibrant flows from first delay chamber 36 through passage 52 into second delay chamber 38; and (4) chamber 94 empties through passage 104, exit port 90, entry port 76 and passage 78 into waste chamber 58.

Next, the cartridge 10 is rotated 90° counter clockwise back to its second position (FIG. 6d) whereupon simultaneously: (1) the sample flows out of the second sample delay chamber 46 through passage 68, disposable exit port 66 and reusable entry port 88, and via passage 98 into delay chamber 92 where a check is made for cell lysis; (2) the first calibrant flows out of the ISE sub-assembly 96 through passage 102, through pond 93 and into chamber 94; (3) the second calibrant flows from its second delay chamber 38 through short passage 54 into third delay chamber 40; and (4) waste chamber 58 does not empty.

Rotation of the cartridge 90° clockwise back to its upright position (FIG. 6e) for completion of its second "rotate return" cycle, results simultaneously in: (1) flow of the sample from the delay chamber 92 through passages 100 and 101 into ISE sub assembly 96, with excess again flowing over into pond 93 via passage 102; (2) flow of the first calibrant from the chamber 94 through passage 104, exit port 90, entry port 76, and passage 78 into waste chamber 58; and (3) flow of the second calibrant from its third delay chamber 40 through passage 56 into its fourth and final delay chamber 42.

Figure 6D:
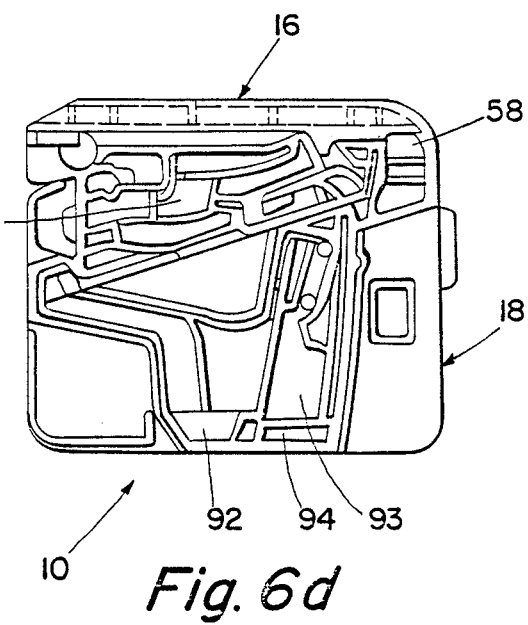
Figure 6E:
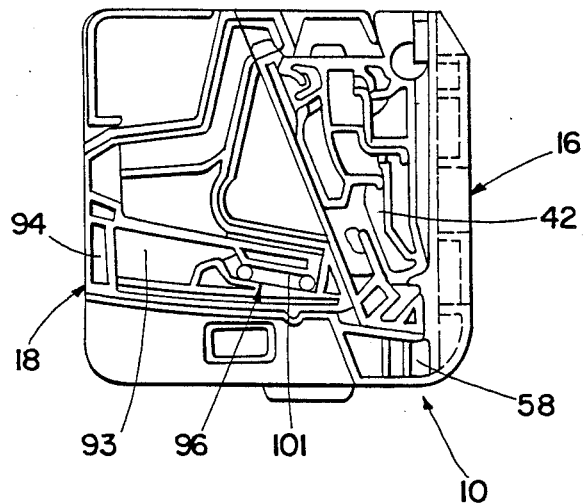
Figure 6F:
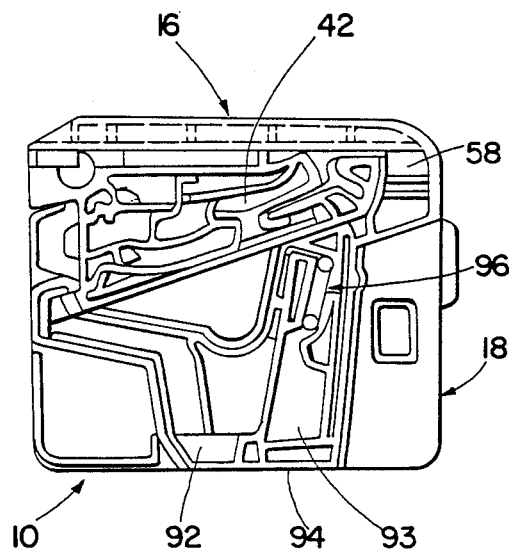

As shown in FIG. 6f, counterclockwise rotation of the cartridge 10 through 90° into its second angular position for the third and last time results simultaneously in: (1) flow of the sample out of the ISE sub-assembly 96 and pond 93 into the holding chamber 94; and (2) flow of the second calibrant from its fourth delay chamber 42 through passages 70 and 68, to disposable exit port 66 and reusable entry port 88, and through passage 98 into delay chamber 92, the first calibrant being retained in the waste chamber 58.

Final clockwise rotation of the cartridge 10 through 90° back to its initial upright position (FIG. 6g) to complete its third "rotate return" cycle results in simultaneous: (1) flow of the sample from the holding chamber 94 through passage 104, and into the waste chamber 58 as before; and (2) flow of the second calibrant from delay chamber 92 through passage 100 into the ISE sub assembly 96 and, via passage 102, into pond 93. Second calibrant is left in the pond area of the reusable to provide a reservoir of solution to keep the sensors moist. For improved stability, it is preferable to choose a second calibrant having a composition approximating that of the electrode fill solutions.

Figure 6G:
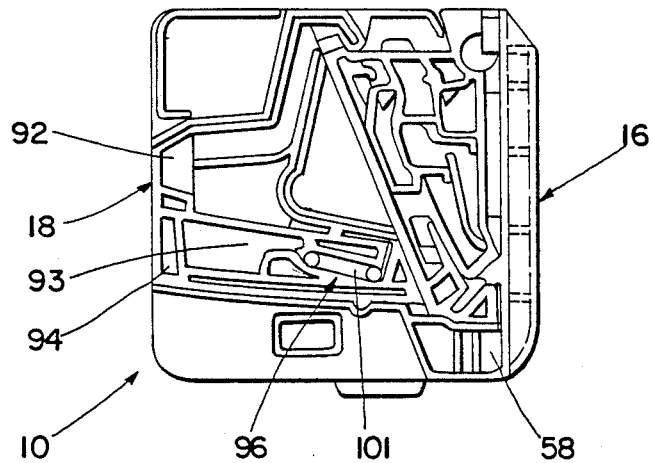

Test data as to the particular electrolyte being assayed is detected and measured by the ISE at three spaced intervals. First, when the first calibrant is in the ISE sub assembly 96 (FIG. 6c); second, when the sample is in the ISE sub-assembly 96 (FIG. 6e); and third, when the second calibrant is in the ISE sub-assembly 96 (FIG. 6g). Hemolysis data is also taken when the sample is in delay chamber 92 (FIG. 6d). Typically, analog signals of the ISE sub assembly 96 are converted to digital signals and are read by an optical system of a type well known in the art. These "readings" correspond respectively to the completion of the first, second and third "rotate return" cycles of the test cartridge 10.

By using the two-part test cartridge 10 disclosed herein whereby one part 16, which includes the waste chamber 58, is disposable and the other part 18, which incorporates the more costly elements of the test cartridge 10, is reusable. The cost of testing for the presence of and measurement of the concentration of various electrolytes in blood/blood serum samples is greatly reduced. With known-type testing apparatus, each sample test may be completed in approximately seven minutes and a centrifuge rotor of such an apparatus can normally accommodate ten test cartridges 10 at one time.

While there has been shown and described a preferred embodiment of the invention, it will be obvious to those skilled in the art that changes and modifications may be made without departing from the invention, and it is intended by the appended claims to cover all such changes and modifications as fall within the true spirit and scope of the invention. For example, it is conceivable to replace the ISE sensors with other sensors responsive to sample and calibrant solutions.

We claim:

1. A two part test cartridge comprising a first disposable cartridge portion having a series of compartments and passageways including a sample entry port, an exit port, a return port leading to a chamber, and one or more calibrant chambers, and a second reusable cartridge portion interengageable with said first cartridge portion and having a series of compartments and passageways including an entry port adapted to interfit with said exit port of said first cartridge portion and an exit port adapted to interfit with said return port of said first cartridge portion to facilitate fluid flow from said disposable portion into said reusable portion and then back to said disposable portion, said reusable cartridge portion further comprising an ion selective electrode circuit.

2. A two-part test cartridge as recited in claim 1 wherein sealing means is provided for each calibrant chamber and wherein means is provided on said second reusable cartridge portion for automatically unsealing each calibrant chamber in said first disposable cartridge portion upon interengagement of said first and second cartridge portions.

3. A two-part test cartridge as recited in claim 1 wherein interfitting key means are provided on said two cartridge portions to insure that the proper disposable portion is used with a correspondingly dedicated reusable portion.

4. For use with a reusable portion of a test cartridge having sample-component sensing means and a network of fluid receiving compartments and passageways, wherein said sensing means comprises an ion sensitive electrode, a power supply and circuitry therefor, a disposable portion interengageable with said reusable portion comprising a sample entry port, filled calibrant chamber means, a waste chamber, and a network of compartments and passageways adapted for communication with said network in said reusable portion for fluid flow back and forth between said disposable and said reusable portions.

5. A disposable test cartridge portion as recited in claim 4 wherein said filled calibrant chamber means are provided with pierceable closure means adapted to be pierced by piercing means provided on said reusable portion upon interengagement thereof.

6. For use in a two-dimensional centrifugal analysis apparatus, an improved test cartridge of the type having a sample entry port, filled calibrant chamber means, sample-component sensing means, a waste chamber, and a series of compartments and passageways, said improvement comprising said cartridge being formed in two interengageable parts, one part being reusable and having said sensing means, wherein said sensing means comprises an ion sensitive electrode, and a portion of said compartments and passageways provided therein, and said other part being disposable and having said sample entry port, said filled calibrant chamber means, said waste chamber, and the remainder of said compartments and passageways provided therein, whereby sample and calibrant fluid flow is back and forth between said two interengageable parts.

7. An improved two-part test cartridge as recited in claim 6 wherein said cartridge includes means for shielding at least said sensing means from interfering electrical noise.

8. An improved two-part test cartridge as recited in claim 6 wherein said filled calibrant chamber means in said disposable part are provided with pierceable closures, and wherein said reusable part is provided with piercing means for piercing said pierceable closure means upon interengagement of said disposable and reusable parts.

9. In a centrifugable cartridge, a disposable portion adapted to interfit with a reusable portion having a sample-component sensing means wherein said sensing means is a sensing electrode, and a series of sample receiving compartments and passageways, said disposable portion comprising a labyrinth of compartments and passageways including a sample entry port, a waste chamber, filled calibrant chamber means, wherein certain of said passageways are adapted to communicate with certain of said passageways of said reusable portion for fluid flow back and forth between the two portions.

10. A disposable test cartridge portion as recited in claim 9 wherein said calibrant chamber means is characterized by pierceable sealing means adapted to be pierced by piercing means on said reusable portion.

11. A disposable centrifugable test cartridge portion comprising a generally planar main member, a housing formation projecting from a portion of said main member, a series of chambers and passageways provided in said housing formation including filled calibrant chamber means, a waste chamber, and passage means adapted to communicate with fluid passage means provided in a second reusable test cartridge portion adapted to be juxtaposed against said main member in interfitting engagement with said housing formation to facilitate fluid flow back and forth between the two test cartridge portions.

12. A disposable test cartridge portion as recited in claim 11 wherein pierceable sealing means is provided for said filled calibrant means, said sealing means adapted to be pierced by piercing means provided on said second reusable test cartridge portion.

* * * * *

UNITED STATES PATENT AND TRADEMARK OFFICE
CERTIFICATE OF CORRECTION

PATENT NO. : 4,940,527

DATED : July 10, 1990

INVENTOR(S) : V. Kazlauskas, et al.

It is certified that error appears in the above-identified patent and that said Letters Patent is hereby corrected as shown below:

```
Col. 1, Lines 41-42, "Industries" should read --Industrie--.
Col. 4, Line 60, "portions" should read --portion--.
Col. 5, Line 26, "funnel like" should read --funnel-like--.
Col. 6, Line 35, "fluids" should read --fluidics--.
Col. 8  Line 24, "rotate return" should read --rotate-return--.
Col. 8, Line 38, "sub assembly" should read --sub-assembly--.
Col. 8, Line 47, "rotate return" should read --rotate-return--.
```

Signed and Sealed this

Thirty-first Day of December, 1991

Attest:

HARRY F. MANBECK, JR.

*Attesting Officer*            *Commissioner of Patents and Trademarks*